United States Patent [19]

Barels et al.

[11] 4,411,885

[45] Oct. 25, 1983

[54] VITAMIN E OIL BASED DENTIFRICE

[76] Inventors: Ronald R. Barels, 1755 Kennington, Leucadia, Calif. 92024; Daniel J. Ghinazzi, 1374 Mossy Ct., Concord, Calif. 94521

[21] Appl. No.: 360,140

[22] Filed: Mar. 22, 1982

Related U.S. Application Data

[60] Continuation-in-part of Ser. No. 242,129, Mar. 9, 1981, abandoned, which is a division of Ser. No. 192,465, Sep. 30, 1980, Pat. No. 4,292,304.

[51] Int. Cl.³ ..................... A61K 7/18; A61K 31/355
[52] U.S. Cl. .......................... 424/52; 424/49; 424/284
[58] Field of Search ................. 424/49–58, 424/284

[56] References Cited

U.S. PATENT DOCUMENTS

| | | | |
|---|---|---|---|
| 1,551,638 | 9/1925 | Brady . | |
| 1,933,977 | 11/1933 | Harris | 167/93 |
| 2,024,146 | 12/1935 | Crowther | 424/49 |
| 2,089,529 | 10/1937 | Behr | 167/93 |
| 2,090,437 | 8/1937 | Woldman | 424/53 |
| 3,431,339 | 3/1969 | Gyarmathy et al. | 424/52 |
| 3,475,533 | 10/1969 | Mayrand | 424/57 |
| 3,538,230 | 11/1970 | Pader et al. | 424/50 |
| 3,551,559 | 12/1970 | Miles | 424/49 |
| 3,574,824 | 4/1971 | Echeandia et al. | 424/50 |
| 3,885,028 | 5/1975 | Cella et al. | 424/52 |
| 3,992,519 | 11/1976 | Hofmann et al. | 424/48 |
| 4,069,311 | 1/1978 | Mannara | 424/49 |
| 4,153,680 | 5/1979 | Seybert | 424/49 |
| 4,169,885 | 10/1979 | Raaf et al. | 424/16 |
| 4,226,851 | 10/1980 | Sompayrac | 424/53 |
| 4,292,304 | 9/1981 | Barels et al. | 424/37 |

OTHER PUBLICATIONS

Robert J. Peshek, DDS, *Dental Examiner,* Vitamin E and tooth decay, Jun. Issue, 1978, p. 2A.

Fedorov, et al., *Chem. Abstr.,* vol. 70 #10293g (1969), Prevention of Experimental Caries in Rats by Administration of Vitamin . . . E . . . NaF Paste.

Schneider et al., *Chem. Abstr.* vol. 71 #36757g (1969), Effects of Vitamin E on the Formation and the Structure of Enamel and Denton.

Lawrence J. Machlin, *Vitamin E, a Comprehensive Treatise,* vol. 1 (1980) marcel dekker, inc., NY, NY, pp. 580–584, 599, 619.

*Primary Examiner*—Shep K. Ross
*Attorney, Agent, or Firm*—Majestic, Gallagher, Parsons & Siebert

[57] ABSTRACT

The present invention provides a tableted dentifrice comprising a compact mass of a substantially anhydrous composition having vitamin E, a surfactant agent and an abrasive agent suitable for removal of plaque. The substantially anhydrous composition has at least about 10 weight percent vitamin E therein.

11 Claims, 1 Drawing Figure

VITAMIN E OIL BASED DENTIFRICE

This is a continuation-in-part of Ser. No. 06/242,129, filed Mar. 9, 1981, now abandoned, which is a division of Ser. No. 06/192,465, filed Sept. 30, 1980, issued Sept. 29, 1981, U.S. Pat. No. 4,292,304.

BACKGROUND OF THE INVENTION

1. Field of the Invention

The present invention generally relates to an oil based dentifrice, and more particularly to a vitamin E oil based dentifrice which may be encapsulated in an edible capsule or formed as a tablet.

2. Prior Art

Anhydrous toothpastes including an oil component are known. For example, U.S. Pat. No. 3,574,824, issued Apr. 13, 1971, inventors Echeandia, et al., discloses an anhydrous toothpaste having an oil component in an amount up to about 35 weight percent which may be used as a vehicle for water incompatible enzymes and the like. U.S. Pat. No. 2,089,529, issued Aug. 10, 1937, inventor Behr, discloses an anhydrous, acidic toothpaste having an oil component in an amount of about 49 weight percent.

Among the disadvantages with prior known, anhydrous toothpastes having oil components therein have been an unpleasant mouth feel when used, often interpreted as an oily sensation, and a reduced shelf life with respect to conventional, hydrous toothpastes due to the tendency of the oil component to oxidize and become rancid.

SUMMARY OF THE INVENTION

Accordingly, it is an object of the present invention to provide a dentifrice which includes a vitamin E oil base resistant to oxidation, which has little or no oily sensation when utilized for oral hygiene, and which also includes sufficient of an abrasive component to assist in the removal of plaque.

It is a further object of the present invention to provide such a vitamin E oil based dentifrice in an encapsulated or a tablet form. The encapsulated or tableted form is preferably of a size and shape suitable for consumption in one use.

These and other objects and advantages are provided in one aspect of the present invention by a substantially anhydrous oil based dentifrice with vitamin E in an amount of at least about 1 weight percent and an abrasive agent in an amount sufficient to assist in the removal of plaque, and which is encapsulated by a water soluble, edible capsule.

In another aspect of the present invention, a substantially anhydrous, vitamin E oil based dentifrice includes vitamin E in an amount of at least about 10 weight percent, an abrasive agent in an amount sufficient to assist in the removal of plaque, and which is tableted. The vitamin E is preferably in the acetate, or solid, form.

DETAILED DESCRIPTION OF THE PREFERRED EMBODIMENTS

Figure 1:
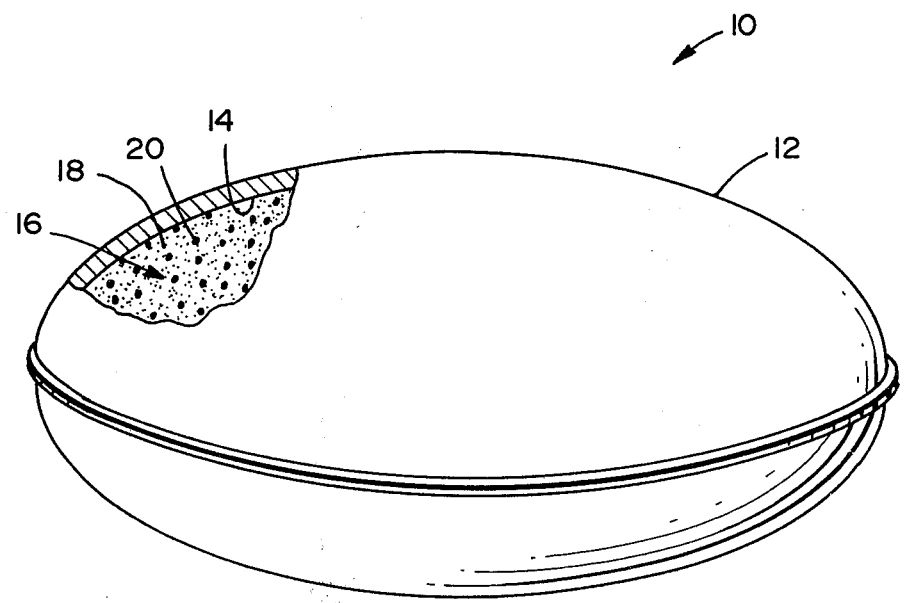
FIG. 1 is a perspective, enlarged view of an encapsulated dentifrice embodiment in accordance with the present invention.

The present invention includes two preferred embodiments, both of which include substantially anhydrous, oil based dentifrice compositions having vitamin E therein. One embodiment is an encapsulated dentifrice and the other is a tableted dentifrice embodiment.

Encapsulated Embodiment

FIG. 1 illustrates an encapsulated dentifrice embodiment 10 in accordance with the present invention which includes a capsule 12 having an interior chamber 14. An oil based dentifrice composition 16 is within interior chamber 14 and is encapsulated by capsule 12. By encapsulation is meant that capsule 12 normally contains dentifrice composition 16 without leakage therefrom until dentifrice embodiment 10 is utilized for tooth cleansing.

Capsule 12 is formed of an edible material which is substantially water soluble but is oil insoluble. A preferred material for capsule 12 is gelatin of sufficient hardness to permit the encapsulation and to resist rupture during handling, packaging, and shipping of dentifrice embodiment 10.

Capsule 12 is preferably adapted to be placed into the user's mouth and be readily crushed between the teeth to release a quantity of dentifrice composition 16 for tooth cleansing. The ruptured capsule 12 may be chewed and/or swallowed. Dentifrice composition 16 is anhydrous and thus does not leak from, or permeate, the oil insoluble capsule 12. Unlike hydrous toothpastes or gels, an oil base 18 of dentifrice composition 16 readily flows about the teeth when capsule 12 is crushed, and thus dentifrice composition 16 is easily dispersed throughout the oral cavity, with or without the aid of a toothbrush or the like. An abrasive agent 20 of dentifrice composition 16 is suspended by oil base 18, and is carried with oil base 18 into contact with tooth areas susceptible to plaque formation. Abrasive agent 20 aids in the removal, or dispersal, of plaque, particularly when dentifrice embodiment 10 is utilized in conjunction with dental floss or the like.

The preferred quantity of dentifrice composition 16 encapsulated by each capsule 12 is suitable for one oral treatment, normally from about 0.5 g to about 1 g, and this preferred quantity shall hereinafter sometimes also be referred to as a "dose". Encapsulated dentifrice embodiment 10 may be readily packaged in foil, plastic or the like, and dispensed to travellers or guests for their convenient use.

The oil based dentifrice composition 16 encapsulated by capsule 12 includes the oil base 18 having a sufficient quantity of a source of vitamin E so as to provide at least about 10 mg. of vitamin E per dose. However, oil based dentifrice composition 16 need not be encapsulated by edible capsule 12, but may be packaged and used in a conventional manner.

The oil base 18 is in a weight ratio with respect to the abrasive agent 20 of from about 1:8 to about 8:1, more preferably a weight ratio greater than about 1:1. Oil base 18 is at least about 10 wt.% of dentifrice composition 16, more preferably is the major component of the dentifrice composition 16, and most preferably is from about 60 weight percent to about 85 weight percent of the total composition.

The oil based dentifrice composition 16 shall now be more fully described.

The oils which may comprise the oil base of the dentifrice composition 16 are edible, are preferably chosen from the various vegetable oils in their natural, or unsaturated, state, and are liquid at room temperature (that is, above about 40° F.). A particularly preferred vegetable oil is safflower oil.

It has been discovered that the inclusion of a sufficient quantity of a source of vitamin E in the oil base of the dentifrice composition 16 substantially reduces or eliminates the oil sensation, or unpleasant mouth feel, of the oil base and tends to reduce oxidation of the oil base. This is particularly important where the oil base constitutes the major component of the dentifrice composition.

It is also believed that inclusion of vitamin E in the oil base of the dentifrice composition 16, in the presence of a quantity of abrasive agent, assists in providing beneficial oral health of the tissues adjacent a user's teeth, usually in conjunction with the removal of plaque by means such as a toothbrush, dental floss or the like. That is, it is believed that the inclusion of a sufficient source of vitamin E in the oil base is of assistance as part of an oral health program for users with gingival irritations, and may be useful following oral surgery, or for users with incipient gum deterioration.

A sufficient quantity of a source of vitamin E in the oil base to substantially reduce or eliminate the oily sensation, or unpleasant mouth feel, of the oil base is wherein the source of vitamin E provides at least about 1 weight percent of vitamin E with respect to the dentifrice composition. Where the dentifrice composition is encapsulated so as to include a predetermined quantity, or dose, of the dentifrice composition, then the source of vitamin E preferably provides at least about 10 mg of vitamin E. For example, where the dose is 1 g., then the weight percent of vitamin E in the dentifrice composition will be at least about 1 wt.%; whereas where the dose is 0.5 g., then the weight percent of vitamin E in the dentifrice composition will be at least about 2 wt.%.

An international unit of vitamin E is generally considered to be equal to 1 miligram of standard DL-alphatocopheryl acetate. Although vitamin E (also known as alphatocopherol) is present in very small concentration (1.0–0.3%) in wheat germ, corn, sunflower seed, rape seed, and soy bean oil, a use of such oils, by themselves, does not result in sufficient quantities of vitamin E for providing the source of vitamin E.

Commercial, edible sources of vitamin E are available, usually as oils, in various international unit amounts. These commercially available sources of vitamin E frequently include various extender oils, usually vegetable oils, such as corn flower oil and the like. Such commercially available sources of vitamin E are suitable for use as the source of vitamin E in the oil base of the present invention, so long as such commercial preparations are utilized in the formation of the present invention so as to provide at least about 1 wt.% of vitamin E in the oil based dentifrice composition, or at least about 10 mg vitamin E per dose when encapsulated.

As will be hereinafter more fully described, the at least 10 weight percent oil base with respect to the total dentifrice composition is preferably provided by vitamin E itself in the tablet embodiment.

Abrasive Agent

The oil based dentifrice composition 16 further comprises an abrasive agent. The abrasive agent of the oil based dentifrice composition 16 should be present in a sufficient amount and be of sufficient abrasiveness so as to aid in the control of plaque when the dentifrice composition is used in conjunction with a toothbrush, dental floss or the like. Where the dentifrice composition is intended for daily use, the abrasiveness should not be excessive, that is, should not abrade tooth enamel over extended periods of use.

It is believed that a sufficient quantity of abrasive agent may be as little as 3 weight percent of the dentifrice's total weight, because of an abrasive-enhancing effect of the abrasive agent in the presence of the oil base. A more preferred quantity of the abrasive agent in the oil based dentifrice composition 16 is from about 5 weight percent to about 35 weight percent with respect to the total composition weight. Larger amounts of the abrasive agent, particularly wherein the amount of abrasive agent exceeds a weight ratio with respect to the oil base of about 1:1, may tend to result in excessive abrasion, or lead to settling out of the abrasive agent, which is normally and desirably suspended in the oil based dentifrice composition.

Sufficient abrasion for daily use is wherein the abrasive agent has a radioactive dentine abrasion value of from about 100 to about 500. Suitable abrasive agents include, for example, calcium carbonate, dicalcium phosphate, calcium pyrophosphate, calcium sulphate, sodium metaphosphate, aluminum silicate, silica xerogels, and silica hydrogels. Such suitable surfactant agents may likewise be utilized in the tablet embodiment in substantially the same amounts.

The oil based dentifrice composition of both embodiments is preferably anhydrous. Several compounds suitable as abrasive agents in the present invention are available in both anhydrous as well as hydrous forms. The hydrous forms are where the water is bound. Although several of these compounds may thus contain bound water, which can usually be driven off by the application of sufficient heat, this water is normally not freely available in the composition. Accordingly, such bound water forms of abrasive agents are suitable for inclusion in the dentifrice compositions and encapsulation by capsule 12 or tableting.

Surfactant Agent

It is desirable that the dentifrice compositions in accordance with the present invention include a surfactant agent as a component thereof. The surfactant component functions as a foaming or sudsing agent for the compositions when exposed to water, or saliva, in the mouth during use. A variety of conventionally known surfactant agents, including non-ionic, cationic and anionic surfactants, for use in the oral cavity are suitable for inclusion into the dentifrice composition. For example, cetyl pyridinium fluoride, bis-2-hydroxyethylalkylamineoxide, sodium lauryl sulfate, and fatty acid esters of sodium isethionate, are suitable as the surfactant component. Various naturally derived compounds having foaming properties, such as the saponins, are also suitable as the surfactant agent. Sodium lauryl sulfate (SLS) is a preferred surfactant agent, either by itself or as a mixture with another surfactant. A mixture of SLS and another surfactant is particularly preferred, as the foaming and sudsing functions of SLS, by itself, tend to be inhibited by the oil base. The amount of surfactant agent is preferably an amount in the range of from about 3 weight percent to about 15 weight percent of the total composition.

Other Components

The inventive compositions may include oral health agents, particularly of the fluoride type, for example sodium fluoride, lithium fluoride, stannous fluoride, potassium fluoride, ammonium fluoride, sodium fluorstanide, stannous chlorofluoride, or sodium monofluorophosphate. Stannous fluoride is a particularly preferred source of fluoride.

Additional components such as sweeteners, flavoring oils and coloring agents may also be incorporated, for example saccharin, peppermint oil, spearmint oil, clove oil, chlorophyll and the like. The quantity of a sweetening component such as saccharin will normally be quite small, as saccharin has a relatively low oil solubility.

EXAMPLES

Ten oil based dentifrice compositions 16 in accordance with the present invention were prepared and are illustrated by Table I below.

TABLE I

| Component | Wt. % | |
|---|---|---|
| Composition 1 | | |
| Vit. E oil (13.5 I.U./cc) | 80.6 | (1.3 of vit. E) |
| Hydrous silica gel* | 7.0 | |
| C$_9$H$_{19}$Ø-0(CH$_2$CH$_2$O)N—CH$_2$OH | 8.0 | |
| Sodium lauryl sulfate | 3.0 | |
| Stannous fluoride | 0.4 | |
| Saccharin/flavoring oil | 1.0 | |
| Composition 2 | | |
| Vit. E oil (118.4 I.U./cc) | 75.5 | (10.6 of vit. E) |
| Hydrous silica gel* | 15.0 | |
| Myristic acid-2-sulfoethyl ester | 6.0 | |
| Sodium lauryl sulfate | 2.0 | |
| Stannous fluoride | 0.3 | |
| Saccharin/flavoring oil | 1.2 | |
| Composition 3 | | |
| Vit. E. oil (13.5 I.U./cc) | 77.5 | (1.2 of vit. E) |
| Hydrous silica gel* | 12.0 | |
| Monocarboxyl Coco imidazoline | 6.0 | |
| Sodium lauryl sulfate | 1.0 | |
| Stannous fluoride | 0.3 | |
| Saccharin/flavoring oil/colorant | 2.8 | |
| Composition 4 | | |
| Vit. E oil (13.5 I.U./cc) | 62.6 | (1.0 of vit. E) |
| Hydrous silica gel* | 25.0 | |
| Coconut acid ester of sodium isethionate | 9.5 | |
| Stannous fluoride | 0.4 | |
| Saccharin/flavoring oil/colorant | 2.6 | |
| Composition 5 | | |
| Safflower oil | 70.0 | |
| Vit. E. oil (126.8 I.U./cc) | 8.6 | (1.3 of vit. E) |
| Hydrous silica gel** | 11.8 | |
| Myristic acid-2-sulfoethyl ester, sodium salt | 5.7 | |
| Sodium lauryl sulfate | 2.7 | |
| Stannous fluoride | 0.3 | |
| Saccharin/flavoring oil | 1.0 | |
| Composition 6 | | |
| Vit. E. oil (13.5 I.U./cc) | 78.6 | (1.3 of vit. E) |
| Silica aerogel*** | 11.8 | |
| Myristic acid-2-sulfoethyl ester, sodium salt | 5.7 | |
| Sodium lauryl sulfate | 2.7 | |
| Sodium fluoride | 0.3 | |
| Saccharin/flavoring oil | 1.0 | |
| Composition 7 | | |
| Vit. E. oil (25.4 I.U./cc) | 42.0 | (1.3 vit. E) |
| Hydrous Silica Gel | 10.0 | |
| Silica Xerogel | 9.4 | |
| Silica Aerogel | 25.2 | |
| Myristic Acid-2 sulfoethyl ester, sodium salt | 8.3 | |
| Sodium lauryl sulfate | 2.2 | |
| Sodium fluoride | 0.4 | |
| Saccharin/Flavoring oil | 2.5 | |
| Composition 8 | | |
| Vit. E. oil (42.3 I.U./cc) | 25.0 | (1.2 vit. E) |
| Hydrous Silica Gel | 11.8 | |
| Silica Xerogel | 3.2 | |
| Silica Aerogel | 49.4 | |
| Myristic Acid-2 sulfoethyl ester, sodium salt | 6.4 | |
| Sodium lauryl sulfate | 1.9 | |
| Sodium fluoride | 0.3 | |
| Saccharin/Flavoring oil | 2.0 | |
| Composition 9 | | |
| Vit. E Oil (109.9 I.U./cc) | 9.9 | (1.3 vit. E) |
| Hydrous silica gel | 15.5 | |
| Silica Xerogel | — | |
| Silica Aerogel | 63.8 | |
| Coconut fatty acid-2 sulfoethyl ester sodium salt | 8.0 | |
| Sodium lauryl sulfate | 1.0 | |
| Sodium fluoride | 0.3 | |
| Saccharin/Flavoring oil | 1.5 | |
| Composition 10 | | |
| Vit. E. oil (13.5 I.U./cc) | 80.9 | (1.3 vit. E) |
| Silica Xerogel | 8.5 | |
| Myristic acid-2 sulfoethyl ester, sodium salt | 7.0 | |
| Sodium lauryl sulfate | 1.5 | |
| Sodium fluoride | 0.3 | |
| Saccharin/Flavoring oil | 1.8 | |

*Total bound water = 31%, RDA = 500, particle size about 12 micron
**Total bound water = 45%, RDA — 500, particle size about 11 micron
***Particle size about 3 micron All of the compositions illustrated by Table I, above, provided an oil based dentifrice composition 16 with little or no oily sensation in the mouth. Each was readily dispersed in the user's mouth, and displayed an excellent debriding action upon food material between the teeth and upon plaque in conjunction with routine flossing and/or brushing. Compositions 1–6 and 10 displayed excellent suspension of the abrasive agent in the oil base. The abrasive component of compositions 7, 8 and 9 however, tended to settle out from suspension in the oil base due to the relatively larger amount of abrasive agent and relatively lower amount of oil.

A first composition substantially equivalent to composition 2, above, was formulated and encapsulated by 1 gram doses into gelatin capsules (so as to provide about 106 mg vitamin E/dose). A second composition, substantially equivalent to composition 4, above, was formulated and encapsulated by 1 gram doses into gelatin capsules (so as to provide about 10 mg vitamin E/dose). A control composition analogous to composition 4, above, but wherein safflower oil entirely replaced the vitamin E oil, was formulated and encapsulated by 1 gram quantities into gelatin capsules (so as to provide substantially no vitamin E/dose). These three compositions were then utilized by thirty dental patients having mild gingival irritations as follows.

A first group of ten patients was instructed to brush twice daily (morning and evening) with a dose at each brushing, the doses having the first composition therein, and to floss once daily. A second group of ten patients was given identical instructions, but these patients were brushing with the second composition. A third group of ten patients was likewise given identical instructions, but these patients were brushing with the control composition. (None of the patients knew the identity of the formulations). After thirty days, all thirty patients were examined. The gums of 29 patients were found to have improved, with the first group having the most improvement, followed by the second group, and the least improvement displayed by the control group. One patient (from the second group) showed little or no improvement which was believed due to extremely poor overall oral hygiene and to not having followed directions. The modest, but general, improvement of the control group may be due to a placebo effect, and/or to generally better oral hygiene during the test period.

Preparation of dentifrice compositions 16 in accordance with the present invention may be where the components are simply admixed. The abrasive agent 20 is readily suspended in oil base 18 when the weight ratio of abrasive agent to oil base is not greater than about 1:1. Thereafter, the dentifrice composition 16 may be encapsulated by edible capsule 12, for example by various conventional encapsulating means, to form the dentifrice embodiment 10.

Tableted Embodiment

The tableted dentifrice embodiment is similar to the encapsulated dentifrice composition embodiment in being adapted to be placed into the user's mouth and to be readily crushed between the teeth to provide a quantity of dentifrice composition for tooth cleansing (e.g. one "dose"). The dentifrice composition of the tablet embodiment preferably further includes one or more excipients to aid in tableting and then in dispersal of the necessary vitamin E and abrasive components in the oral cavity during use, and preferably utilizes vitamin E neat and in the amounts previously described for the oil base where such is a source of vitamin E.

That is, the quantity of vitamin E of the tableted dentifrice composition is in an amount of at least 10 weight percent of the total composition, and thus the oil base is preferably neat vitamin E, such as in the acetate form, which solidifies from the viscous, oily liquid state at temperatures above about −27.5° C. At quantities which provide less than about 10 wt.% of α-tocopherol acetate in the tableted, total dentifrice composition, there is a loss of smooth, or waxy, mouth feel.

It is also believed that the inclusion of vitamin E in the tableted form, in the presence of a quantity of abrasive agent, assists in providing beneficial oral health of the tissues adjacent a user's teeth in an analogous manner to the vitamin E of dentifrice composition 16 in the encapsulated embodiment. Suitable excipients include for example, sorbitol, glycols, glycerol derivatives, polyglycerols, polyglycerol esters and the like for providing emulsifying, lubricating and/or dispersing functions in the dentifrice composition. Particularly preferred are admixtures of a major amount of sorbitol and minor amounts of calcium or magnesium stearate.

As with the encapsulated embodiment, each tablet of the tableted embodiment is preferably of a size and shape suitable for one oral treatment, normally from about 0.5 g to about 1 g, and may be readily packaged individually in foil, plastic or the like, and dispersed to travellers or guests for their convenient use. A suitable abrasive agent, as previously described, is carried with the vitamin E into contact with tooth areas susceptible to plaque formation.

Four vitamin E oil based dentifrice compositions in accordance with the present invention were prepared, as illustrated by Table II, below.

TABLE II

| Component | Wt. % |
|---|---|
| Composition 11 | |
| Vit. E oil (neat α-tocopherol acetate) | 49.0 |
| silica aerogel | 9.0 |
| sorbitol | 34.5 |
| sodium lauryl sulfate | 2.0 |
| coconut acid ester of sodium isethionate | 1.0 |
| calcium stearate | 0.5 |
| sodium bicarbonate | 2.0 |
| citric acid | 1.0 |
| flavoring oil | 0.5 |
| stannous fluoride | 0.5 |
| Composition 12 | |
| Vit. E oil (neat α-tocopherol acetate) | 59.0 |
| silica xerogel | 7.0 |
| sorbitol | 29.0 |
| sodium lauryl sulfate | 2.0 |
| coconut acid ester of sodium isethionate | 1.0 |
| calcium stearate | 1.0 |
| flavoring oil | 0.5 |
| stannous fluoride | 0.5 |
| Composition 13 | |
| Vit. E oil (neat α-tocopherol acetate) | 16.0 |
| silica aerogel | 9.0 |
| silica xerogel | 5.0 |
| sodium lauryl sulfate | 3.0 |
| sorbitol | 62.0 |
| sodium bicarbonate | 3.0 |
| calcium stearate | 0.5 |
| citric acid | 1.5 |
| flavoring oil (wintergreen) | 0.5 |
| stannous fluoride | 0.5 |
| Composition 14 | |
| Vit. E oil (neat α-tocopherol acetate) | 23.0 |
| silica aerogel | 14.5 |
| sorbitol | 58.0 |
| sodium lauryl sulfate | 2.5 |
| coconut acid ester of sodium isethionate | 0.5 |
| magnesium stearate | 0.5 |
| flavoring oil | 0.5 |
| stannous fluoride | 0.5 |

The above four compositions were readily compacted into discrete mass, or tablet, of from about 650 mg to about 850 mg by means of a conventional tableting press. The tablets were easily crushed and dispersed throughout the oral cavity with or without the aid of a toothbrush or the like, but were of sufficient hardness to resist friability during handling, packaging and shipping.

In summary, the preferred dentifrice compositions, which include a source of vitamin E in the presence of an abrasive agent, result in a unique product for oral health care. Further, the dentifrice embodiments provide a particularly convenient, easily dispensed article for use by travellers or the like.

While the invention has been described in connection with specific embodiments thereof, it will be understood that is is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A vitamin E oil based dentifrice composition formed as an edible tablet adapted to be placed in a user's mouth and readily crushed, said tablet having
an abrasive agent in an amount of from about 3 weight percent to about 35 weight percent with respect to said tablet,
a quantity of vitamin E, said plurality of vitamin E in an amount of about 10 weight percent to about 85 weight percent with respect to said tablet,
a surfactant agent in a sufficient amount of said tablet to provide sudsing when said tablet is crushed and then agitated in the presence of an aqueous solution, and,
at least one excipient component.

2. The dentifrice composition as in claim 1 wherein:
said vitamin E is α-tocopheryl acetate, and said surfactant agent is in an amount of at least about 3 weight percent.

3. The dentifrice composition as in claim 1 wherein the at least one excipient component includes a minor amount of an oral health agent providing a source of fluoride therein.

4. The dentifrice composition as in claim 1 wherein:
said abrasive agent is selected from the group consisting of calcium carbonate, dicalcium phosphate, calcium pyrophosphate, calcium sulphate, silica xerogel, silica aerogel and mixtures thereof.

5. The dentifrice composition as in claim 1 wherein said surfactant agent includes sodium lauryl sulfate.

6. The dentifrice composition as in claim 1 wherein the at least one excipient component includes a major amount of sorbitol.

7. A tableted composition prepared by the process comprising:
admixing vitamin E acetate, an adhesive agent, a surfacant agent, and at least one excipient component to provide a dentifrice composition, the composition having at least about 10 wt. percent vitamin E acetate, and from about 3 to about 35 weight abrasive agent; and,
compacting the dentifrice composition to form a substantially anhydrous discrete mass.

8. The tableted composition as in claim 7 wherein:
the at least one excipient component includes a major amount of sorbitol.

9. The tableted dentifrice composition as in claim 8 wherein:
the at least one excipient includes a minor amount of an oral health agent providing a source of fluoride therein.

10. The tableted dentifrice composition wherein:
the surfactant agent includes sodium lauryl sulfate.

11. The tableted dentifrice composition as in claim 7 wherein:
the discrete mass formed in the compacting is from about 0.5 g to about 1 g.

* * * * *

UNITED STATES PATENT AND TRADEMARK OFFICE
CERTIFICATE OF CORRECTION

PATENT NO. : 4,411,885
DATED : Oct. 25, 1983
INVENTOR(S) : Barels et al.

It is certified that error appears in the above-identified patent and that said Letters Patent is hereby corrected as shown below:

Col. 9, line 9: "plurality" should read --quantity--.

Signed and Sealed this

Twelfth Day of June 1984

[SEAL]

Attest:

GERALD J. MOSSINGHOFF

Attesting Officer    Commissioner of Patents and Trademarks